(12) United States Patent
Bratkovski et al.

(10) Patent No.: US 8,664,940 B2
(45) Date of Patent: Mar. 4, 2014

(54) GRAPHITE-BASED SENSOR

(75) Inventors: Alexandre M. Bratkovski, Mountain View, CA (US); Iakov Veniaminovitch Kopelevitch, Mountain View, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 650 days.

(21) Appl. No.: 12/902,480

(22) Filed: Oct. 12, 2010

(65) Prior Publication Data

US 2012/0086439 A1   Apr. 12, 2012

(51) Int. Cl.
*G01N 27/74* (2006.01)
*G01R 33/07* (2006.01)
*G01R 33/02* (2006.01)

(52) U.S. Cl.
USPC ............................ 324/204; 324/244; 324/251

(58) Field of Classification Search
USPC .................................................. 324/204, 251
See application file for complete search history.

(56) References Cited

U.S. PATENT DOCUMENTS

2008/0237533 A1   10/2008   Araujo Moreira et al.
2010/0007979 A1   1/2010   Tsukada

OTHER PUBLICATIONS

Collins et al., "Extreme Oxygen Sensitivity of Electronic Properties of Carbon Nanotubes", Science, Mar. 2000, pp. 1801-1804, vol. 287, University of California at Berkeley.
Dai et al., "Adsorption of Molecular Oxygen on Doped Graphene: Atomic, Electronic and Magnetic Properties", Nov. 24, 2009, pp. 1-8, Department of Physics, National University of Defense Technology, Changsha 410073, People's Republic of China.
Owens, "Effect of Oxidation of Graphene Nanoribbons on Electronic and Magnetic Properties", Molecular Physics, Nov. 2008, pp. 2441-2443, vol. 106, Hunter College, New York.
Lee et al., "Magnetism in Graphite Oxide: The Role of Epoxy Groups", Jun. 1, 2010, pp. 1-6.
Wojtaszek, "Exploring Magnetism in Graphene", Physics of Nanodevices, University of Groningen, pp. 1-16.
Xing et al, "Strong Correlation Between Ferromagnetism and Oxygen Deficiency in Cr-Doped In2O3-? Nanostructures", Physical Review B, May 5, 2009, vol. 79.
Zhao et al., "Electrical Transport and Magnetic Properties of La0.5Ca0.5MnO3-y With Varying Oxygen Content", Physical Review B, Mar. 21, 2002, pp. 144406-1-144406-6, vol. 65.

*Primary Examiner* — Bot Ledynh

(57) ABSTRACT

A graphite-based sensor includes an undoped graphite structure that adsorbs foreign atoms and molecules. A magnetization detection device includes a substrate on which the graphite structure is adhered, a current source by which a current is applied to the substrate and the graphite structure, and a voltage measuring device coupled to the substrate. When the graphite structure adsorbs the gas molecules, the graphite structure exhibits a ferromagnetic-type behavior, and a corresponding voltage generated in the magnetic detection device changes.

15 Claims, 3 Drawing Sheets

GRAPHITE-BASED SENSOR

BACKGROUND

At high temperatures, carbon-based materials are known to exhibit ferromagnetic properties. More recently, carbon-based materials have been shown to exhibit ferromagnetism (FM) at room temperatures. More specifically, recent experiments have shown that absorbed atoms/molecules can trigger room temperature ferromagnetism in carbon structures. However, whether this ferromagnetic behavior is intrinsic to the carbon-based materials, or extrinsic (e.g., caused by metallic impurities) is not fully understood.

DESCRIPTION OF THE DRAWINGS

The Detailed Description will refer to the following drawings, in which like numerals refer to like items, and in which.

DETAILED DESCRIPTION

Carbon-based materials have reportedly demonstrated ferromagnetic behavior under certain conditions. For example, ferromagnetism in carbon samples at high temperatures reportedly has been demonstrated for over two decades. However, this behavior generally is believed to be related to metallic impurities in the carbon structure. More recently, experiments involving carbon samples have demonstrated ferromagnetic behavior at room temperature. These experiments provide evidence that absorbed foreign atoms and molecules can trigger room temperature ferromagnetism. In one experiment, room temperature ferromagnetism was reportedly induced in fullerene crystals by exposing them to light irradiation from a xenon lamp in the presence of oxygen. In another experiment, a graphite powder sample obtained from bulk graphite reportedly revealed a ferromagnetic response when the sample was exposed to an oxygen atmosphere.

Figure 1:
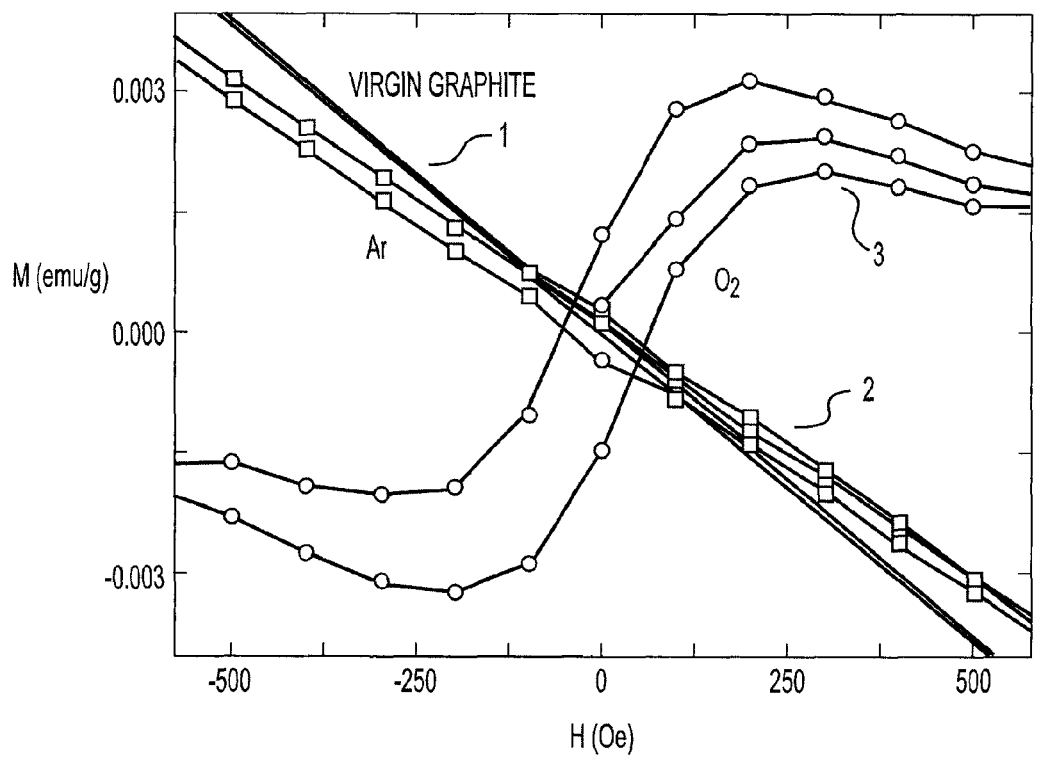
FIG. 1 illustrates magnetic moment versus applied magnetic field of a carbon sample exposed to certain gases.

A herein disclosed graphite-based sensor uses the ferromagnetic behavior of carbon structures, including at or near room temperature, to detect the presence of gases and liquids. FIG. 1 illustrates this ferromagnetic behavior. In FIG. 1, magnetic moment M (in emu/g) is graphed versus magnetic field strength H (in Oe). A virgin graphite sample (curves 1) was exposed to an argon (Ar) gas atmosphere. As used herein, virgin graphite means graphite samples without any dopant atoms. In addition, a graphite powder sample (curves 2), also obtained from virgin graphite, was exposed to an Ar atmosphere. The plotted data show a negative slope, indicating a diamagnetic behavior for both samples. Also shown in FIG. 1 (curves 3) is the magnetic moment of a graphite powder sample exposed in an oxygen atmosphere. In the oxygen atmosphere, the graphite powder sample demonstrates a pronounced ferromagnetic-type hysteresis loop. Similar results were obtained for graphite powder samples in other gas environments, including helium, nitrogen and hydrogen gas environments.

The mechanism that produces this ferromagnetic-type behavior is the apparent adsorption of certain gas atoms/molecules in a carbon structure. For example, in an oxygen atmosphere, $O_2$ molecules may be adsorbed in the lattice structure of the carbon sample. Following this adsorption, and as long as the $O_2$ remains adsorbed, the carbon sample will demonstrate a magnetic response similar to that shown in curves 3 of FIG. 1.

Figure 2:
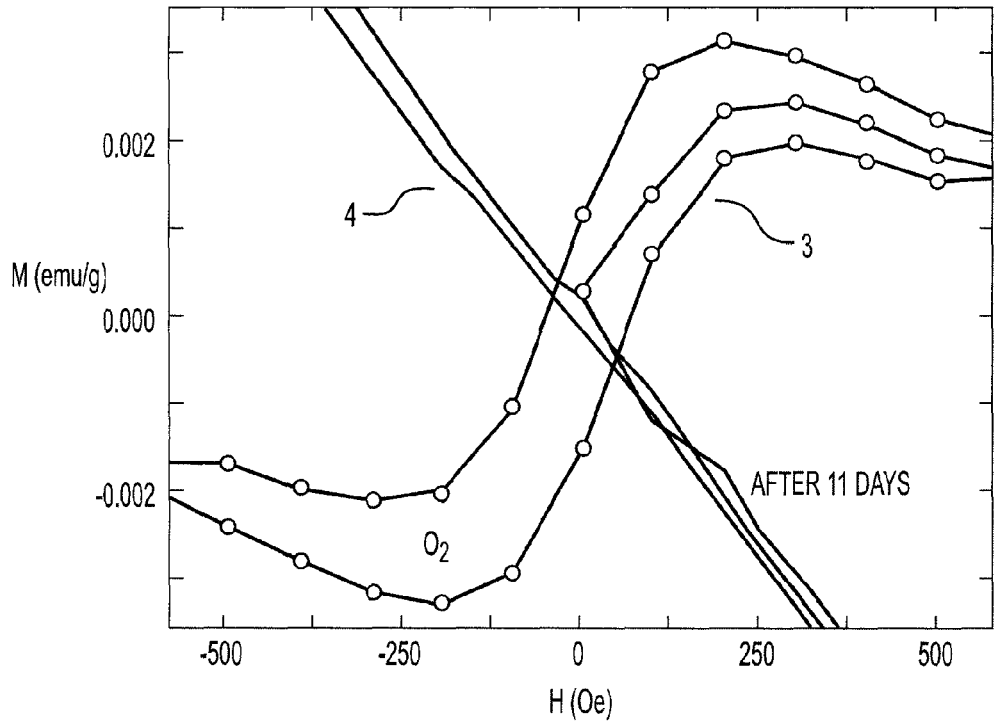
FIG. 2 illustrates magnetic moment for a carbon sample immediately after exposure to a gas atmosphere, and after removal of the carbon sample from the gas atmosphere.

Upon de-adsorption of the gas atoms/molecules (e.g., $O_2$), the ferromagnetic behavior exhibited by the carbon structure will disappear. This behavior is shown in FIG. 2, which like FIG. 1, shows magnetic moment versus magnetic field strength. In FIG. 2, curves 3 show the characteristic ferromagnetic behavior of a carbon structure having adsorbed oxygen molecules. However, if the oxygen-bearing atmosphere is removed from the carbon structure (or the carbon structure removed from the oxygen bearing atmosphere), then, after a time (in the example shown in FIG. 2, eleven days), the ferromagnetic-type hysteresis loop relating magnetic moment and magnetic field strength returns to the diamagnetic behavior as shown in the curves 4. Alternately, the carbon structure may be "annealed" by heating to drive out the oxygen molecules. Such heating may more rapidly restore the carbon structure to a state in which no or few foreign atoms and molecules are retained in the carbon structure than simply removing the sensor from the environment being monitored.

Physically, what is believed to occur in producing the ferromagnetic-type hysteresis behavior is that the carbon structure exhibits magnetization on its "edges," but the magnetization along two parallel edges is opposite in effect, such that the net magnetization of the carbon structure is zero. The adsorption of oxygen molecules (or other specific gases) on an edge further "upsets" this zeroing balance. When a transverse electric field is applied to such a carbon structure, it reacts differently on oppositely oriented spin states at opposite edges of the carbon structure. The electrostatic potential on one edge is lowered and on the opposite edge is raised. Correspondingly, the energies for localized edge states on one edge are shifted upwards and on the opposite edge are shifted downwards, eventually leaving states of only one spin orientation and producing the displayed ferromagnetic-like behavior shown in FIGS. 1 and 2. When the oxygen molecules are removed (e.g., the carbon structure is annealed), the diamagnetic behavior returns.

Thus, it appears that the adsorption/desorption of certain gases at a graphite surface are responsible for the appearance and disappearance of ferromagnetic-like behavior of graphite structures, and accordingly, such ferromagnetic-like behavior appears to be related to the entrapment of gas atoms/molecules at graphite defect sites.

Figure 3:
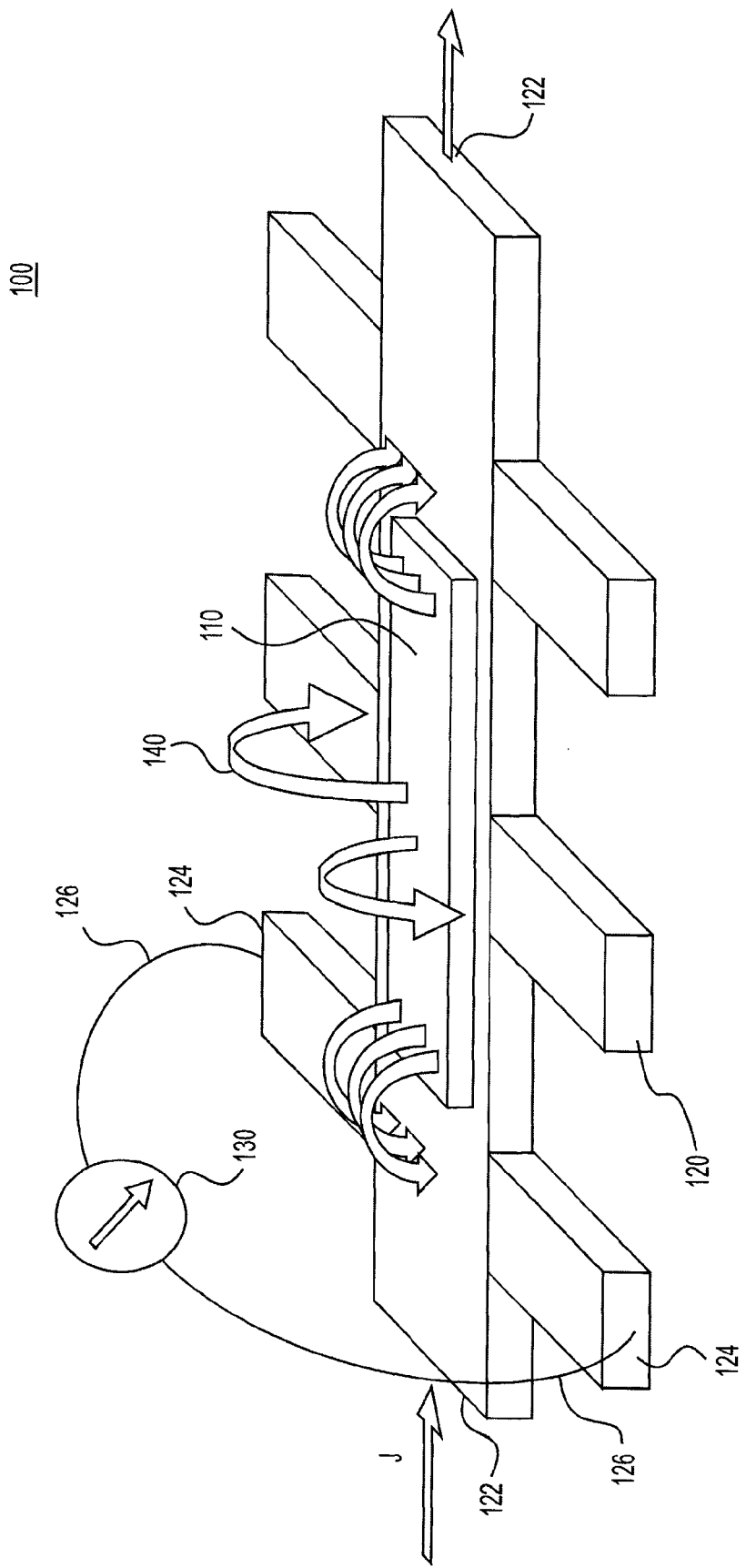
FIG. 3 illustrates an example of a graphite-based sensor.

Because certain carbon structures exhibit this ferromagnetic-like behavior upon adsorption of certain gases, a properly constructed carbon structure may be used in a gas or liquid sensor. FIG. 3 illustrates an embodiment of a graphite-based sensor that may be used to detect the presence of certain atoms/molecules in a fluid environment. One specific application of the graphite-based sensor is to detect the presence of certain gases in an atmosphere. Examples of gases that may be detected, and their concentration measured (inferred), using this graphite-based sensor include oxygen ($O_2$), sulfur (S), and bromine (Br). In addition, through a calibration process, an embodiment of which is described below, the graphite-based sensor can be used to identify a specific atom/molecule and quantify the amount (concentration) of atoms present (e.g., the concentration of a specific gas present in the atmosphere). The graphite-based sensor example shown in FIG. 3, and described below is inexpensive, has a small form factor, produces reliable, reproducible results, is reusable, and is operable at room temperatures.

In FIG. 3, graphite-based sensor 100 includes a graphite structure 110 that is coupled to a magnetic detection device 120, which in the illustrated example, is a Hall bar, although available magnetometers could be used in place of the Hall bar 120. The Hall bar 120 may be formed from silicon, and may be generally rectangular is shape. Current electrodes 122 may be used to apply a transverse, alternating current to the Hall bar 120, and voltage electrodes 124 may be used to read out the voltage induced (i.e., the Hall voltage), using voltage detector 130, connected to the electrodes 124 by wires 126. When the graphite structure 110 adsorbs certain gases, the structure 110 exhibits a ferromagnetic-like behavior, as indicated by arrows 140, which in turn, upon application of current to the electrodes 122, induces the Hall voltage. Thus, the presence of an induced Hall voltage on the voltage detector 130 indicates the presence of certain gases in the environment in which the graphite-based sensor 100 has been placed.

The graphite structure 110 may be any suitable carbon device, including a few layers-thick (FLG) graphene device cleaved from a virgin graphite sample, and graphite powder (obtained by cleaving and grinding a virgin graphite sample), for example. In an example in which graphite powder is used, the structure 110 may include a container that holds the graphite powder. The structure 110 has a small form factor, on the order of approximately one cubic millimeter. However, sensitivity of the graphite-based sensor is affected to some degree by the size (e.g., surface area) of the structure 110, with larger surface-area structures being more sensitive. The structure 110 may be supported by a substrate, such as a silicon-based device. In an example, the structure may be supported by a silicon Hall bar, as noted above. In this example, the Hall bar 120 not only supports the structure 110 but also is used to measure the magnetization that results when the structure 110 adsorbs certain foreign atoms or molecules. In other examples, other known magnetization measuring devices may be used with the graphite-based sensor. For example, commercially available devices, including the superconducting quantum interference device (SQUID) from Quantum Design, torque, VSM, and other types of magnetometers may be used for these magnetization measurements.

The graphite-based sensor 100 may be used only for sensing the presence of certain atoms/molecules in a fluid. However, the sensor 100 may be used in a calibrated sensing system to not only detect the presence of these atoms/molecules, but also to determine the concentration of these atoms/molecules in the fluid (assuming some nominal distribution of the fluid within the environment being monitored). More specifically, a graphite based sensor 100 may be calibrated by exposing the sensor 100 to various known gas concentrations and measuring the resulting magnetization, M (emu/g). The resulting magnetization/gas concentration data then may be used in a sensor that, for example, detects the presence of certain gases, provides an input to an alarm function, and an input to a properly programmed processor to report gas identity and concentration.

A calibrated graphite-based sensor as disclosed herein will produce a differing Hall voltage in response to an applied current in the presence of adsorbed foreign atoms/molecules in the graphite structure because the magnetization of the graphite structure changes in the presence of the adsorbed foreign atoms/molecules. In an example, a calibrated graphite-based sensor may be used to detect the presence of a specific gas. Additionally, the graphite-based sensor may be used to provide inputs to other devices that can be used subsequently for an alarm function and a gas concentration readout function. In another example, a graphite-based sensor may be used to detect the presence of certain atoms/molecules in a liquid environment.

Figure 4:
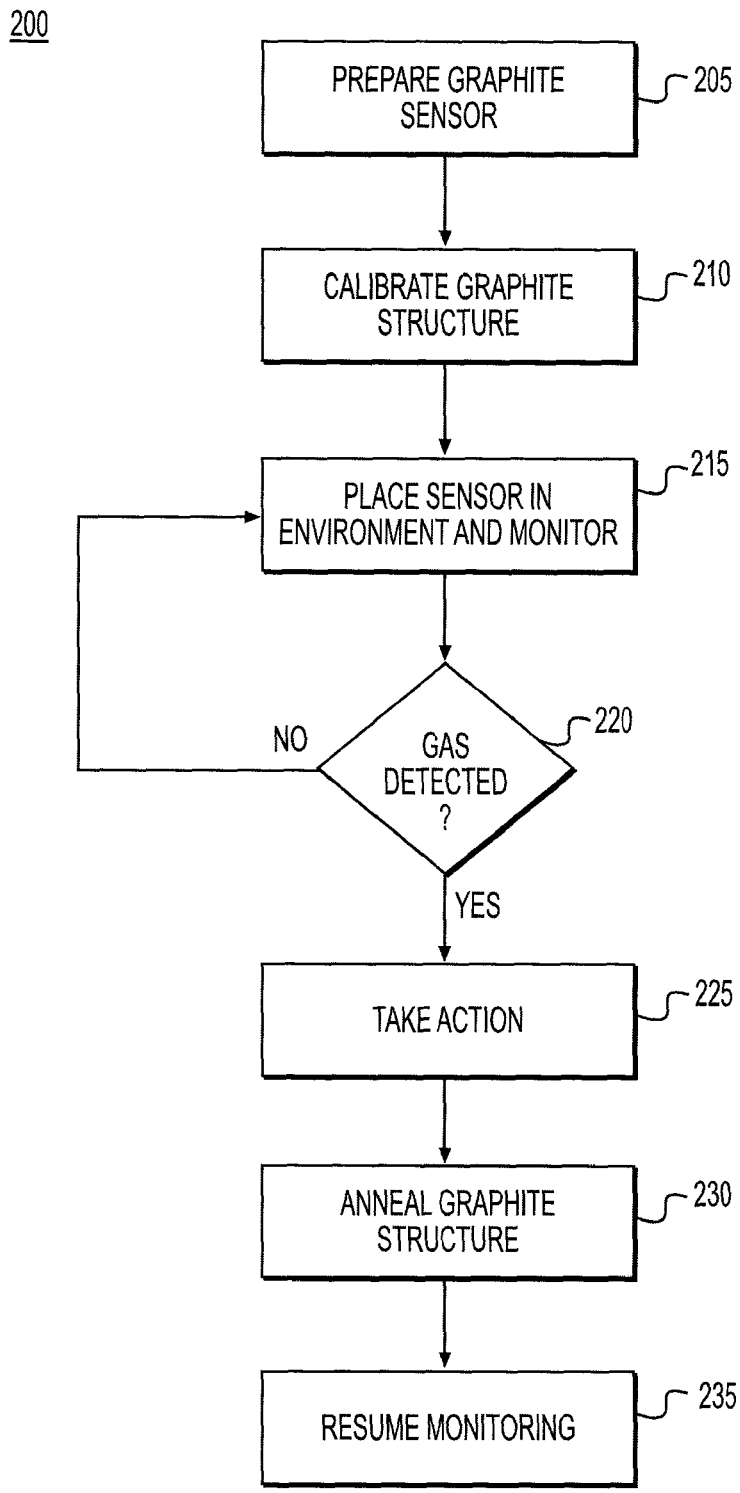
FIG. 4 is a flowchart illustrating an example of an operation of the graphite-based sensor of FIG. 3.

FIG. 4 is a flowchart illustrating an example of an operation of the graphite-based sensor 100 of FIG. 3. In FIG. 4, the sensor 100 may be used to detect the presence of certain gases in an environment. In FIG. 4, operation 200 begins in block 205 when graphite-based gas sensor 100 is prepared for use. The preparation may include preparations for installation of the sensor 100 in the environment. The sensor 100 includes undoped graphite structure 110, which may be few layers-thick graphene or graphite powder. The preparation may optionally include forming the sensor 100 by emplacing the structure 110 on a substrate such as a silicon Hall bar. Alternately, the sensor 100 is packaged for installation and use in the desired environment, and the preparation of block 205 includes determining a location for the sensor 100. In block 210, the sensor 100 may be calibrated to ensure it is capable of detecting the desired gas or gasses of interest, and capable of providing a signal that may be used to identify a specific gas, and its concentration, in the environment. Such calibration may be conducted in situ or prior to delivery to the environment being monitored.

In block 215, the sensor 100 may be emplaced at the designated location, connected to appropriate monitoring readout and alarm devices, and placed in operation such that monitoring of the environment using the sensor 100 begins. To begin monitoring, a current may be applied to the Hall bar 120. Then, a corresponding Hall voltage may be read out. The Hall voltage changes based on the magnetization of the graphite structure 110, and the magnetization (ferromagnetic-type behavior) of the graphite structure 110 changes (from diamagnetic to ferromagnetic, for example) when the structure 110 adsorbs certain gases. In block 220, if a threshold concentration of the specific gas or gasses being monitored is not reached (N), the operation 200 continues with the monitoring of block 215. If, however, in block 220, the threshold concentration is reached (Y), the operation 200 moves to block 225.

In block 225, some specified action (sound alarm, send report, display gas species and concentration) may be completed. Following the specified action, in block 230, the sensor 100, and more specifically the graphite structure 110, may be "annealed." Such annealing may take the form of heating to drive off the adsorbed gas or gasses. Alternately, the environment may be ventilated or otherwise evacuated to remove the gas or gasses, or the sensor 100 may be removed from the environment. In any of these options, the adsorbed gas or gasses may be desorbed, and the sensor may then be reused for detecting the gas or gasses. After the annealing of block 230, the sensor 100 is returned to the environment (if removed) or otherwise is placed back in operation and monitoring is resumed.

Certain of the steps noted above may not be used. For example, the calibration process may not be used when only the detection of a gas or gasses is desired. As another example, the calibration may be completed in situ. Other modifications to the operation 200 are possible.

We claim:
1. A graphite-based sensor, comprising:
   an undoped graphite structure formed to adsorb foreign atoms and molecules; and
   a magnetic detection device, comprising:
   a substrate on which the graphite structure is adhered,
   a current source by which a current is applied to the substrate and the graphite structure, and a voltage measuring device coupled to the substrate, wherein when the graphite structure adsorbs the gas molecules, the graphite structure exhibits a ferromagnetic-type behavior, and a corresponding voltage generated in the magnetic detection device changes.

2. The graphite-based sensor of claim 1, wherein the foreign atoms and molecules are gas atoms and molecules.

3. The graphite-based sensor of claim 2, wherein the gas atoms and molecules include oxygen, bromine, sulfur, and nitrogen.

4. The graphite-based sensor of claim 1, wherein the foreign atoms and molecules are liquid atoms and molecules.

5. The graphite-based sensor of claim 1, wherein the graphite structure comprises few layers-thick graphene (FLG).

6. The graphite-based sensor of claim 1, wherein the graphite structure is a graphite powder (GP) structure, and wherein the graphite-based sensor further comprises a container mechanism that contains the GP structure.

7. The graphite-based sensor of claim 1, wherein the substrate is a Hall bar.

8. The graphite-based sensor of claim 1, wherein the graphite-based sensor is calibrated to provide an output to identity and concentration of the foreign atoms/molecules.

9. The graphite-based sensor of claim 1, wherein the graphite structure has a form factor of 1 cubic millimeter.

10. The graphite-based sensor of claim 1, wherein when the foreign atoms and molecules are desorbed, the magnetization returns to diamagnetic.

11. A graphite-based sensor, comprising:
an undoped graphite structure that adsorbs foreign atoms and molecules, wherein the adsorption changes a magnetic behavior of the graphite structure from diamagnetic to ferromagnetic-like behavior; and
a magnetization sensing device coupled to the undoped graphite structure that measures the magnetization of the undoped graphite structure.

12. The graphite-based sensor of claim 11, wherein the magnetization sensing device is a silicon Hall bar.

13. The graphite-based sensor of claim 11, wherein the virgin graphite structure comprises few layers-thick graphene (FLG).

14. The graphite-based sensor of claim 11, wherein when the foreign atoms and molecules are desorbed, the magnetic behavior of the graphite-based sensor changes to diamagnetic.

15. The graphite-based sensor of claim 11, wherein the graphite-based sensor is calibrated to provide an indication of atom/molecule identity and concentration.

* * * * *